(12) United States Patent
Tunac

(10) Patent No.: US 10,449,209 B2
(45) Date of Patent: *Oct. 22, 2019

(54) METHODS AND COMPOSITIONS FOR REVERSING DISRUPTION OF THE GLYCOCALYX, INFLAMMATION, AND OXIDATIVE DAMAGE

(71) Applicant: Arterez, LLC, Metamora, MI (US)

(72) Inventor: Josefino B. Tunac, Oxford, MI (US)

(73) Assignee: ARTEREZ, LLC, Metamora, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/117,808

(22) PCT Filed: Apr. 20, 2016

(86) PCT No.: PCT/US2016/028383
§ 371 (c)(1),
(2) Date: Aug. 10, 2016

(87) PCT Pub. No.: WO2016/176089
PCT Pub. Date: Nov. 3, 2016

(65) Prior Publication Data
US 2018/0036285 A1    Feb. 8, 2018

Related U.S. Application Data

(60) Provisional application No. 62/154,426, filed on Apr. 29, 2015.

(51) Int. Cl.
*A61K 31/4045*    (2006.01)
*A61K 31/7052*    (2006.01)
(Continued)

(52) U.S. Cl.
CPC ........ *A61K 31/7052* (2013.01); *A61K 9/0053* (2013.01); *A61K 31/381* (2013.01);
(Continued)

(58) Field of Classification Search
CPC .............. A61K 31/7052; A61K 31/706; A61K 31/385; A61K 9/0053; A61K 31/4045;
(Continued)

(56) References Cited

U.S. PATENT DOCUMENTS 8,410,162 B2    4/2013  Garner et al.
8,759,095 B2    6/2014  Vink et al.
(Continued)

FOREIGN PATENT DOCUMENTS

WO    WO 2005/062893    7/2005
WO    WO 2009/121959    10/2009
WO    WO 2016/176089    11/2016

OTHER PUBLICATIONS

US 8,628,958 B2, 01/2014, Vink et al. (withdrawn)
(Continued)

*Primary Examiner* — Angela C Brown-Pettigrew
(74) *Attorney, Agent, or Firm* — Emily M. Haliday; Weaver Austin Villeneuve & Sampson LLP

(57) ABSTRACT

A composition for treating multiple disease causes including a glycocalyx restoring and maintaining compound. A method of treating multiple disease causes, by administering a glycocalyx restoring and maintaining compound to an individual, restoring the glycocalyx, reversing inflammation, and reversing oxidative damage. A method of treating cardiovascular disease. A method of restoring the glycocalyx. A method of reversing inflammation. A method of reversing oxidative damage. A method of treating any disease involving a membrane that has a glycocalyx. A method of treating multiple disease causes. A method of restoring the structural and functional integrity of receptors in the glycocalyx. A method of restoring the glycocalyx and receptors therein and potentiating drug response. A composition for treating disease including the glycocalyx restoring and maintaining compound and an antibody. A composition for
(Continued)

treating cardiovascular disease including the glycocalyx restoring and maintaining compound and a MAb anti-PCSK9.

41 Claims, 2 Drawing Sheets

(51) Int. Cl.
| | |
|---|---|
| A61K 45/06 | (2006.01) |
| A61K 31/381 | (2006.01) |
| A61K 31/40 | (2006.01) |
| A61K 31/4406 | (2006.01) |
| A61K 31/498 | (2006.01) |
| A61K 9/00 | (2006.01) |
| A61K 31/385 | (2006.01) |
| A61K 31/706 | (2006.01) |
| A61K 39/00 | (2006.01) |

(52) U.S. Cl.
CPC ............ *A61K 31/385* (2013.01); *A61K 31/40* (2013.01); *A61K 31/4045* (2013.01); *A61K 31/4406* (2013.01); *A61K 31/498* (2013.01); *A61K 31/706* (2013.01); *A61K 45/06* (2013.01); *A61K 2039/505* (2013.01); *A61K 2300/00* (2013.01)

(58) Field of Classification Search
CPC .... A61K 45/06; A61K 31/4406; A61K 31/40; A61K 31/381
See application file for complete search history.

(56) References Cited

U.S. PATENT DOCUMENTS

| | | |
|---|---|---|
| 9,867,842 B2 | 1/2018 | Tunac et al. |
| 2002/0058029 A1 | 5/2002 | Hanna |
| 2006/0153912 A1 | 7/2006 | Habich et al. |
| 2007/0129312 A1 | 6/2007 | Yatvin et al. |
| 2014/0357691 A1 | 12/2014 | Garner et al. |
| 2016/0158250 A1 | 6/2016 | Bar-or |
| 2016/0296603 A1 | 10/2016 | Long et al. |
| 2017/0080006 A1 | 3/2017 | Tunac et al. |

OTHER PUBLICATIONS

Wada et al (The Journal of Vitaminology 7, 237-242 (1960)) (Year: 1960).*
U.S. Notice of Allowance dated Sep. 13, 2017 issued in U.S. Appl. No. 15/348,495.
U.S. Notice of Allowance dated Oct. 11, 2017 issued in U.S. Appl. No. 15/348,495.
PCT International Search Report and Written Opinion dated Jul. 22, 2016 issued in PCT/US2016/028383.
PCT International Preliminary Report on Patentability and Written Opinion dated Oct. 31, 2017 issued in PCT/US2016/028383.
Alphonsus et al. (Apr. 2014) "The endothelial glycocalyx: a review of the vascular barrier" *Anaesthesia* 69: 777-784.
Ballantyne et al. (Feb. 2, 2015) "Results of Bococizumab, a Monoclonal Antibody Against Proprotein Convertase Subtilisin/Kexin Type 9, from a Randomized, Placebo-Controlled, Dose-Ranging Study in Stalin-Treated Subjects With Hypercholesterolemia" *The American Journal of Cardiology* 115: 1212-1221.

* cited by examiner

METHODS AND COMPOSITIONS FOR REVERSING DISRUPTION OF THE GLYCOCALYX, INFLAMMATION, AND OXIDATIVE DAMAGE

CROSS-REFERENCE TO RELATED APPLICATIONS

This application is a U.S. 371 National Phase of PCT/US2016/028383, filed Apr. 20, 2016, which claims the benefit of and priority to U.S. Ser. No. 62/154,426, filed Apr. 29, 2015, which is incorporated herein by reference in its entirety for all purposes.

BACKGROUND OF THE INVENTION

1. Technical Field

The present invention relates to methods and compositions for treating diseases involving disruption of the glycocalyx, inflammation, and oxidative damage. More specifically, the present invention relates to methods and compositions for treating cardiovascular disease.

2. Background Art

The existence of the glycocalyx, a thin layer at the endothelial surface was discovered about 40 years ago (1966. Fed Proc 25:1773-1783). However, the significance of this structure was not recognized, partly because it is destroyed upon conventional tissue fixation and not seen in most light microscopic examinations. The glycocalyx is a protective lining at the surface of the endothelium found in every healthy blood vessel; it is made of proteoglycan, a complex network of protein (glycoprotein) and disaccharide sugar (glycosaminoglycan). This complex network (originating from plasma and vessel wall) forms a dynamic layer between the flowing blood and the endothelium, continuously changing in thickness depending on shear or blood flow pressure. Thus, the shear generated by blood flow regulates the balance between biosynthesis and shedding of the various glycocalyx components. The core protein groups of this layer are syndecans and glypicans promiscuously bound with different glycosaminoglycan including heparan sulfate, chondroitin sulfate, dermatan sulfate, keratan sulfate, and hyaluronan (or hyaluronic acid). In the vasculature, heparan sulfate represents roughly 50-90% of the total amount of proteoglycans followed by chondroitin sulfate with a typical ratio of 4:1, respectively (2007.Pflugers Arch; 454: 345-359).

The glycocalyx can also be found on the apical portion of the microvilli within the digestive tract, especially within the small intestine. It creates a meshwork 0.3 micrometers thick and consists of acidic mucopolysaccharides and glycoproteins that project from the apical plasma membrane of epithelial absorptive cells It provides additional surface for adsorption and includes enzymes secreted by the absorptive cells that are essential for the final steps of digestion of proteins and sugars.

Each cell is surrounded by a glycocalyx. The glycocalyx layer of conjoined cells of a tissue form a glycocalyx layer of a tissue's surface and form a barrier. Once disrupted, the underlying cell is susceptible to disruption and immune attack by macrophages and the like. The glycocalyx of endothelial cells, such as the endometrium, the inner surface of the lungs, the microvilli of the kidney, the pancreas, etc., form a cellular seal that cannot be disrupted.

Further, the glycocalyx at the cellular level supports the structural and functional integrity of the glycoproteins and other biomolecules passing there through. Biomolecules that form channels, receptors, and other functional components of the cell membrane structurally and functionally coexist with and through the glycocalyx. Disruption of the glycocalyx results in disruption of the structure and function of those biomolecules, thereby disrupting the structure and function of the cells, as well as the tissues, and organs comprised of those cells.

Other generalized functions effected by status of glycocalyx include protection (it cushions the plasma membrane and protects it from chemical injury), immunity to infection (it enables the immune system to recognize and selectively attack foreign organisms), defense against cancer (changes in the glycocalyx of cancerous cells enable the immune system to recognize and destroy them), transplant compatibility (it forms the basis for compatibility of blood transfusions, tissue grafts, and organ transplants), cell adhesion (it binds cells together so that tissues do not fall apart), inflammation regulation (glycocalyx coating on endothelial walls in blood vessels prevents leukocytes from rolling/binding in healthy states), fertilization (it enables sperm to recognize and bind to eggs), and embryonic development (it guides embryonic cells to their destinations).

Today, the glycocalyx is recognized as a key structure for maintaining vascular wall integrity and proper function of many organs. Disruptions in the glycocalyx can be due to contact with fluid flow. A thick glycocalyx indicates the absence of plaque, found at straight flow and high shear areas. A thin glycocalyx promotes plaque buildup, especially where there is whirlpool blood flow with low shear in vascular bends. Plaques are essentially patches that cover tiny gaps to maintain osmotic balance of membranes. The tiny gaps in the membrane leak electrolytes both into (Na+Cl–, Ca+, HCO3) and out (K+, PO4–, Mg+) of cells which can lead to a number of conditions. Disruptions can also be caused by the presence of oxidants or debris in adjacent fluid.

Any disruption or decrease in thickness of the glycocalyx can result in many different conditions, including chronic vascular disease (2010. Cardiovascular Research. Volume 87, Issue 2 pp. 300-310). For example chronic stagnant blood flow, common in bifurcated sections of the arteries, triggers glycocalyx shedding and plaque formation. In the heart, disrupted glycocalyx in the coronaries result in poor blood flow (coronary perfusion); at the arteriolar level, a damaged glycocalyx slows down blood flow and decreases nitric oxide (NO) production creating constrictive vessel; and, at the capillary level, disrupted glycocalyx reduces blood flow to tissues or muscles. In addition, the glycocalyx harbors a wide array of enzymes that regulate proper blood flow including superoxide dismutase (SOD), an enzyme which neutralizes reactive oxygen species; antithrombin (AT-III), a natural anticoagulant (blood thinner); and, lipoprotein lipase (LPL), an enzyme that releases triglycerides from chylomicrons and very low-density lipoproteins (VLDL) for energy. See FIG. 1.

In case of cardiac ischemia/reperfusion injury (heart muscle damage due to blood flow obstruction, then re-establishment of blood supply), disrupted glycocalyx results in coronary constriction, poor blood flow, and edema. However, pre-treatment of the heart with antithrombin reduces glycocalyx shedding and restores coronary functions (2009. Cardiovascular Research. Volume 83, Issue 2 Pp. 388-396).

Other more general consequences of a disrupted glycocalyx include osmotic gradient shifts, leakage between cells (such as vascular, kidney, and lung cells), macrophage infiltration and inflammation, and tissue dysfunction. Eventually, glycocalyx dysfunction can lead to blockage of flow in vasculature, the kidneys, the pancreas, and other organs and tissue.

Cardiovascular disease (CVD) is the leading disease killer in the world and because of its complexity and manifested clinical sequelae, it continues to be the main subject in pathology research. Although members of the CVD family are totally different in clinical presentations, they are basically atherosclerosis related and share a common feature, which is vascular damage, particularly to the endothelial glycocalyx. Once the vasculature is damaged, the thromboembolism cascade ensues. Thromboembolism as a process leading to the formation of thrombus (blood clot); once this thrombus dislodges from its origin, it forms an embolus, which flows downstream in the blood vessel tree as a thromboembolus and clogs up blood flow. A thrombus is a solid mass consisting of platelets, fibrin and blood components. An embolus is a piece of thrombus broken free and carried into the bloodstream. Thromboembolus is a floating embolus that becomes lodged and blocks blood flow, which is the fatal component in CVD.

The blood pressure generated by the pumping heart fluctuates and blood flow particularly slows down at arterial forks and bends, notably in the coronary arteries. High fat diet increases blood viscosity and further stagnates blood flow; this stagnation creates low shear and consequently shedding or disruption of the endothelial glycocalyx. Glycocalyx thickness range from 2 to 3 μm in small arteries to 4.5 μm in carotid arteries (2007. J Vasc Res 44:87-98) and shedding or damage to this layer decreases protective shield leading to leakage of nutrients (extravasation) and tissue edema, loss of nutritional blood flow, and an increase in coagulability due to platelet and leucocyte clumping (adhesion). Thus, protection and/or restoration of the endothelial glycocalyx presents a promising therapeutic target both in an acute critical care setting and in the treatment of chronic vascular disease. Drugs that can specifically increase the synthesis of glycocalyx components, refurbish it, or selectively prevent its enzymatic degradation are not currently available. (2010. Cardiovascular Research, Volume 87, Issue 2 pp. 300-310).

Under inflammatory conditions the integrity of the endothelial glycocalyx deteriorates to varying degrees particularly during generalized inflammatory responses, but glycocalyx could regain its original thickness after proper treatment of inflammatory condition (2008. Circulation Research, vol. 102, no. 7, pp. 770-776). Thus, therapeutic strategies can be directly aimed at preserving, supporting, or reconstituting the glycocalyx structure or strategies either indirectly by down regulating inflammatory processes or directly by inhibition of glycocalyx degradation with antioxidants (2006. American Journal of Physiology: Heart and Circulatory Physiology, vol. 290, no. 6, pp. H2247-H2256). An example of an anti-inflammatory drug is etanercept (Enbrel), which inhibits TNF-α, and reduces the shedding of glycocalyx constituents, coagulation activation, and functional vessel function in humans (2009. Atherosclerosis, vol. 202, no. 1, pp. 296-303).

Another approach is antithrombin therapy, since thrombin is known to cleave the syndecan component of glycocalyx (2009. Circulation Research, vol. 104, no. 11, pp. 1313-1317). Indeed, antithrombin therapy protects glycocalyx from TNF-α and ischemia/reperfusion-induced shedding in hearts (2009. Basic Research in Cardiology, vol. 104, no. 1, pp. 78-89; 2010. Shock, vol. 34, no. 2, pp. 133-139), which is accompanied by reduced post ischemic leukocyte adhesion in hearts, reduced vascular permeability, reduced coronary leak, and reduced interstitial edema (2009. Basic Research in Cardiology, vol. 104, no. 1, pp. 78-89).

CVD includes a family of diseases affecting both arteries and veins: diseases in the arteries include coronary heart disease (CHD), myocardial infarction (MI), stroke, hypertension, atrial fibrillation, congestive heart failure (CHF), congenital heart condition, and peripheral arterial disease (PAD); diseases in the veins include venous thrombosis, deep venous thrombosis (DVT), and pulmonary embolism (PE).

Coronary heart disease (CHD) results from the effects of atherosclerotic plaque formation in coronary arteries. The reduction in blood supply to the heart muscles reduce the heart's efficiency and can cause heart failure. One of the first and major symptoms of this condition is angina (chest pain caused by reduced blood flow to the heart muscle).

Myocardial infarction (MI), commonly known as heart attack, is the irreversible necrosis of heart muscle due to prolonged interruption of blood supply (ischemia). The heart requires constant supply of oxygen and nutrients; if one of the arteries or branches becomes blocked suddenly, the heart is starved of oxygen, a condition called "cardiac ischemia." If cardiac ischemia lasts too long, the starved heart tissue dies, which is called heart attack (myocardial infarction) literally, "death of heart muscle".

Stroke occurs when brain cells die owing to a lack of blood supply, which may be classified as ischemic or hemorrhagic: ischemic stroke involves decreased blood supply to parts of the brain, leading to brain cell death and thus brain dysfunction; hemorrhagic stroke is due to rupture of blood vessels or abnormal vascular structure, causing accumulation of blood in a part of the brain. The majority of strokes (80%) are ischemic in nature.

Hypertension or high blood pressure is defined as a condition wherein the pressure of the blood flowing through blood vessels remains high for a prolonged period irrespective of the body's need. An increased blood pressure leads the heart to work harder, which makes the heart and arteries more susceptible to injury. Hypertension further increases the risk of incidents such as heart attack, heart failure, and atherosclerosis.

Cardiac arrhythmias are heart rhythm problems, which occur when heartbeats are not well coordinated owing to improper electric impulses. This may cause the heart to beat too fast (tachycardia) or too slowly (bradycardia). Arrhythmias are generally harmless and momentary, but frequent rhythm disturbances increase the risk of stroke and congestive heart failure. Atrial fibrillation is the most common sustained arrhythmia Congestive heart failure (CHF) is a condition wherein the heart fails to supply blood to the various parts of the body. This can be due to narrowed arteries, myocardial infarction, heart valve disease, high blood pressure, cardiomyopathy, or congenital abnormalities.

Peripheral artery disease (PAD) is a vascular disorder in which the thickening of arteries causes reduction in blood flow to limbs, leading to intermittent leg pain while walking. The disease is an indicator of atherosclerosis. It leads to sores (that do not heal) and gangrenes.

Deep Vein Thrombosis (DVT) is a blood clot that usually forms in the deep veins of the lower leg or arm, which can block the venous return. A DVT may cause leg pain or swelling, but can also present no symptoms. DVT is not usually life threatening, but it can be if the blood clot breaks loose and lodges into the lungs. This is known as a pulmonary embolism (PE).

Historically, cardiovascular therapeutic drugs do not, nor are they intended to focus on the cause of CVD, but are focused on developing medicines that target the symptoms of CVD. Strategies currently existing in the marketplace are the development and marketing of symptom-targeted drugs while incidences of cardiovascular disease (CVD) still continue to rise.

There is an array of symptom-targeted drugs currently marketed against cardiovascular disease including cholesterol-lowering drugs such as statins and fibrates for CHD; diuretics, ACE inhibitors, ARBs, calcium inhibitors, and β-blockers for hypertension; and, anti-clotting drugs such as anti-coagulants (e.g. heparin, rivaroxaban, low molecular weight heparin, dabigatran etexilate mesylate, bivalirudin, coumadin, abciximab, eprifibatide, tirofiban), anti-platelets (e.g. clopidogrel bisulfate, prasugrel, ticagrelor, cilostazol, aspirin, terutroban, dipyridamole), and fibrinolytics (e.g. tissue plasminogen activator (tPA), streptokinase) for stroke. However, these therapies at best mask and treat the symptoms (hypertension, lipidemia, clotting) of CVD, and not the root causes. The therapies decrease levels of fibrin or platelets but do not bust or dissolve clots, they cause either excessive bleeding at high doses or clotting at low doses, and they can decrease Vitamin K levels leading to poor calcium control and heart calcification and osteoporosis. Furthermore, some drugs such as statins have risk of serious side effects such as liver damage, type 2 diabetes, prostate cancer, memory loss, confusion, and dementia.

There are also many other therapeutics existing that merely treat symptoms as opposed to root causes of diseases other than CVD. For example, nitroglycerin is administered for angina symptoms such as chest pain in order to open blood vessels and improve blood flow. It is not administered to treat the underlying cause of why the blood vessels are constricted in the first place. Anti-inflammatories (such as aspirin, ibuprofen, and naproxen (NSAIDS—non-steroidal anti-inflammatory drugs)) are administered in order to reduce inflammation or swelling in the body and relieve pain. They are not administered to treat the underlying cause of why the inflammation is present. Analgesics, especially narcotic analgesics (morphine, codeine, oxycodone, and other opiates), are administered to relieve the symptom of pain or severe pain. They are not administered to treat the underlying cause of the pain. One of the few existing therapeutics that treats an underlying cause is antibiotics, which are administered to kill or inhibit the growth of bacteria in the body. The bacteria themselves can present a whole range of symptoms including pain, irritation, and inflammation that go away once the source is eliminated.

There remains a need for a method of restoring and/or maintaining the integrity of the protective glycocalyx lining of the endothelial vessel wall against atherogenic insults to treat CVD and other diseases. There also remains a need for treating the root causes of CVD and other diseases.

SUMMARY OF THE INVENTION

The present invention provides for a composition for treating multiple disease causes including a glycocalyx restoring and maintaining compound.

The present invention provides for a method of treating multiple disease causes, by administering a glycocalyx restoring and maintaining compound to an individual, restoring the glycocalyx, reversing inflammation, and reversing oxidative damage.

The present invention provides for a method of treating cardiovascular disease (CVD), by administering a glycocalyx restoring and maintaining compound to an individual suffering from CVD, restoring the glycocalyx, reversing inflammation, and reversing oxidative damage.

The present invention provides for a method of restoring the glycocalyx by administering the glycocalyx restoring and maintaining compound and restoring the glycocalyx.

The present invention provides for a method of reversing inflammation by administering the glycocalyx restoring and maintaining compound to an individual, reversing inflammation, and restoring the glycocalyx.

The present invention provides for a method of reversing oxidative damage by administering the glycocalyx restoring and maintaining compound to an individual, reversing oxidative damage, and restoring the glycocalyx.

The present invention also provides for a method of treating any disease involving a membrane that has a glycocalyx, by administering the glycocalyx restoring and maintaining compound to an individual, restoring the glycocalyx of the membrane, reversing inflammation, and reversing oxidative damage.

The present invention further provides for a method of treating multiple disease causes, by administering a combination therapeutic to an individual, and targeting multiple causes of a disease.

The present invention provides for a method of restoring the structural and functional integrity of receptors in the glycocalyx by administering the glycocalyx restoring and maintaining compound to an individual, and restoring structural integrity and function of receptors imbedded in and passing through the glycocalyx.

The present invention provides for a method of restoring the glycocalyx and receptors therein and potentiating drug response, by administering the glycocalyx restoring and maintaining compound and an antibody to an individual suffering from disease, restoring the glycocalyx, restoring receptors in the glycocalyx, and potentiating the response of the antibody.

The present invention also provides for a composition for treating disease including the glycocalyx restoring and maintaining compound and an antibody.

The present invention provides for a method of restoring the glycocalyx and receptors therein and potentiating drug response, by administering the glycocalyx restoring and maintaining compound and a MAb anti-PCSK9 to an individual suffering from disease, restoring the glycocalyx, restoring LDL receptors in the glycocalyx, and potentiating the response of the MAb anti-PCSK9.

The present invention also provides for a composition for treating cardiovascular disease including the glycocalyx restoring and maintaining compound and a MAb anti-PCSK9.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
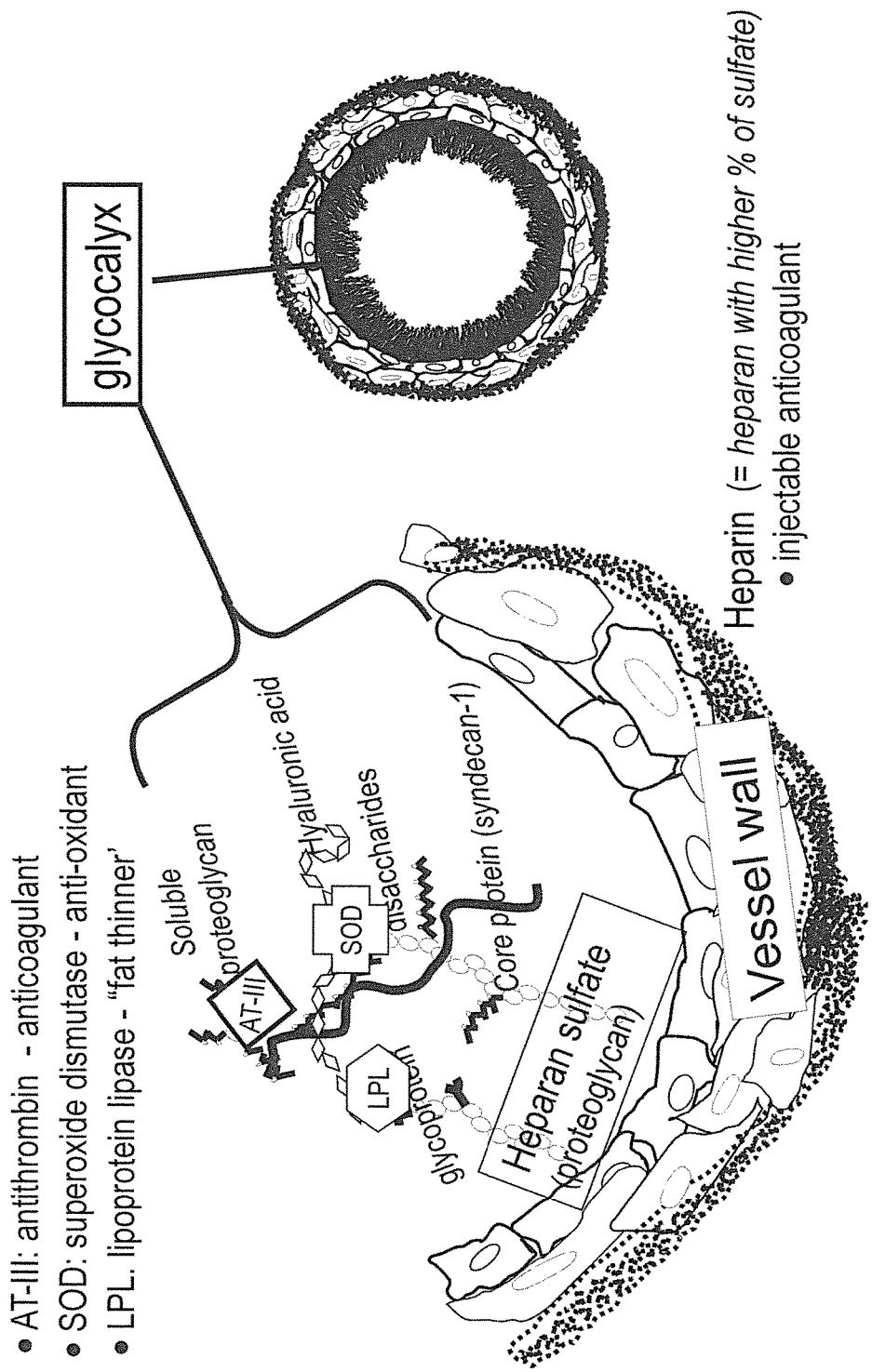
FIG. 1 is a depiction of three enzymes associated with the glycocalyx that regulate blood flow.

The present invention is generally directed to methods and compositions that restore the glycocalyx. Disruption of the glycocalyx is at the root of many diseases, especially CVD. The compositions of the present invention maintain the integrity of glycocalyx in many different membranes.

"Disrupting" or "disruption of" the glycocalyx as used herein refers to any process or disease state that affects the glycocalyx such that it is not functioning normally. Disruption can be caused by inflammation or oxidation in the body. Disruption can cause the glycocalyx to thin and lose its component proteoglycans.

"Inflammation" as used herein refers to a protective response of tissue to injury or destruction in order to eliminate or cordon off any injurious agent and the injured tissue and initiate tissue repair. Inflammation can cause pain, heat, redness, swelling, and loss of function. Inflammatory mediators (cytokines and chemoattractants) can cause shedding of the glycocalyx. Inflammation can also cause leukocytes to degranulate enzymes that can degrade the glycocalyx.

"Oxidative damage", "oxidative stress", or "oxidation" as used herein refers to an imbalance of reactive oxygen species (ROS) and the body's ability to detoxify reactive intermediates and repair damage caused by ROS. Inflammation can cause the release of ROS. The presence of ROS can cause significant damage to cell structures, including the glycocalyx.

"Antioxidant" as used herein refers to a molecule that inhibits the oxidation of other molecules and is able to neutralize or eliminate ROS.

The present invention provides for a composition for treating multiple disease causes of a glycocalyx restoring and maintaining compound. The composition preferably treats disruption of the glycocalyx, inflammation, and oxidative damage. The composition can also treat any one of these causes individually. The glycocalyx restoring and maintaining compound can be any suitable compound that is able to perform these functions in the body.

For example, the glycocalyx restoring and maintaining compound can be a peptide and homolog of the glycopeptides in the glycocalyx that acts to stimulate glycoprotein synthesis. During glycoprotein synthesis, the peptide portion of the molecule is synthesized first, then the sugar moieties are incorporated. Attachment of the peptide portion to the surface appears to be by association between a region of repeated amino acids and components of the glycocalyx.

Most preferably, the glycocalyx restoring and maintaining compound can be a combination of the compounds FTX-214, FTX-218, and FTX-219. Alternatively, the glycocalyx restoring and maintaining compound can be any of the compounds FTX-214, FTX-218, FTX-219, FTX-226-4, FTX-224-2, or FTX-216-4, alone or in combination. Each compound can be effective on its own for the indications described below and for restoring the glycocalyx (and as such they can be used individually in the methods herein), but in combination they can synergistically be used to restore and maintain the glycocalyx, and reverse inflammation and oxidative damage that can be damaging and disrupting the glycocalyx.

FTX-214 is an antioxidant and increases the antioxidative capacity to prevent build-up of reactive oxygen species that damage glycocalyx by boosting the antioxidant enzymes GSH, SOD, and CAT. FTX-214 (melatonin 6,β-D xyloside) is shown in FORMULA I.

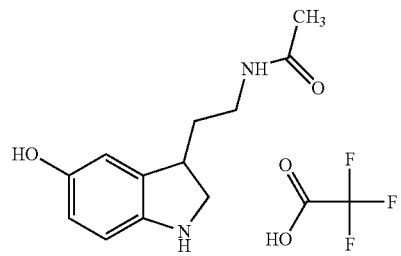

(FORMULA I)

FTX-218 is an anti-inflammatory, neutralizes cytokines, and promotes glycocalyx synthesis. FTX-218 (lipoate-choline) is shown in FORMULA II.

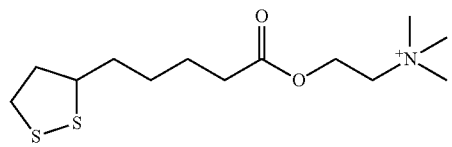

(FORMULA II)

FTX-219 repairs the glycocalyx and restores component building block parts and boosts synthesis of glycocalyx. FTX-219 (lipoate-cysteine-glutamic tripeptide) is shown in FORMULA III.

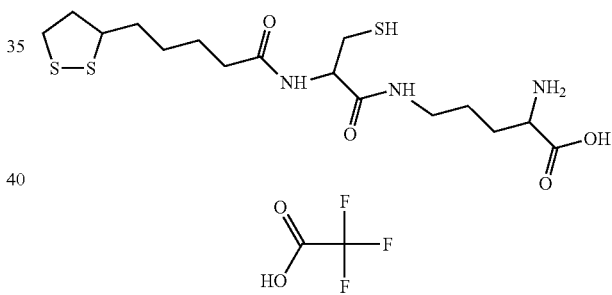

(FORMULA III)

FTX 216-4 has base functionality of 6-N-oxide ribose-phenazinol as exemplified in FORMULA IV.

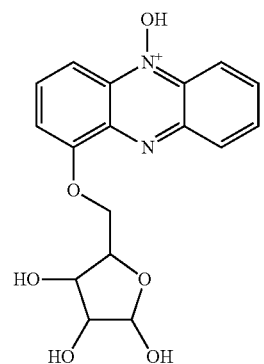

(FORMULA IV)

The composition in FORMULA IV stimulates chondroitin sulfate synthesis, the second most common glycosaminoglycan (GAG) in the endothelial cell glycocalyx. β-D-Xylosides act as primers for GAG chain initiation and compete with the xylosilated core protein, which adds galactose to a xylose residue on the core protein. Xyloside activity varies with the aglycone (since primers compete with endogenous substrates and inhibits proteoglycan (PG) and glycoprotein synthesis, type of aglycone is critical). The composition is a broad spectrum antimicrobial agent.

FTX 224-2 (FORMULA V) (Di Oxide isothiocyanate indole) was designed to inhibit blood clotting.

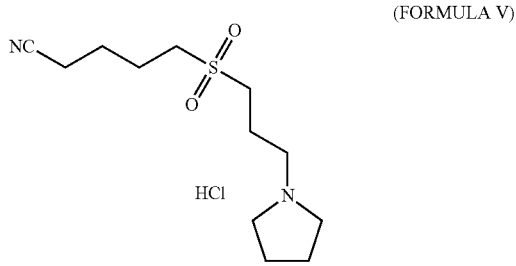 [SMILES: N#CCCCCS(=O)(=O)CCCN1CCCC1 ; Cl]

(FORMULA V)

Also, the compound of FORMULA V acts as an anti-inflammation agent, an antiproliferation agent, and an anti-angiogenesis agent and is known to prevent glutathione depletion in the liver.

FTX 226-4 is a piperidine ribose as exemplified in FORMULA VI.

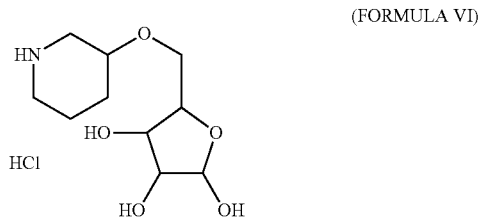 [SMILES: Cl ; OC1OC(COC2CCCNC2)C(O)C1O]

(FORMULA VI)

The compound of FORMULA VI inhibits production of two important proinflammatory mediators, IL6 and PGE2 (triggers pain) and enhances drug bioavailability by inhibiting drug metabolism or by increasing absorption. This compound can be useful in combination treatments with other drugs by improving therapeutic effect or lowering the dose requirements of other drugs when administrated with disease-modifying antirheumatic drugs (DMARDs) as a therapeutic drug or dietary supplement. The compound is an antihypertensive as it inhibits platelet aggregation, and stabilizes and increases activity of eNOS, which leads to decreased blood pressure.

FTX 229 is a nicotinyl choline as exemplified in FORMULA VII.

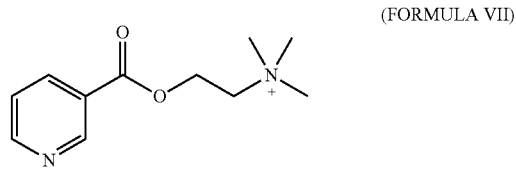

(FORMULA VII)

After the discovery of the nicotinic acid receptor GPR109A on adipocytes and immune cells, novel direct immunomodulatory properties of nicotinic acid have been identified including the release of inflammatory mediators from adipose tissue, direct anti-inflammatory activities of nicotinic acid in other cells previously indicated as key players in atherogenesis (such as hepatocytes andendothelial and vascular cells), nicotinic acid keeps macrophages from entering the atherosclerotic vascular wall by activating its receptor, thereby halting chronic inflammation. On the other hand, choline serves various functions in mammalian bodies: structure of cell membranes, protecting the liver from accumulating fat, as the precursor molecule for the neurotransmitter acetylcholine, and more. Choline via its metabolite, trimethylglycine (betaine), is a major source for methyl groups that participates in the S-adenosylmethionine synthesis pathways, used in treating hepatitis, glaucoma, atherosclerosis, and, possible, neurological disorders.

FTX 230 is an ammonium lipoate as exemplified in FORMULA VIII.

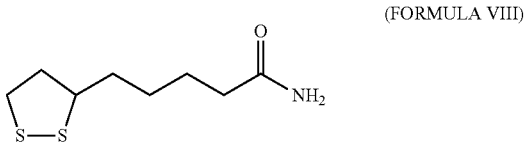 [SMILES: NC(=O)CCCCC1CCSS1]

(FORMULA VIII)

Lipoic acid is reduced to dihydrolipoic acid and serves as an antioxidant. Reduced glutathione (GSH) is the most abundant non-protein thiol in mammalian cells and the preferred substrate for several enzymes in xenobiotic metabolism and antioxidant defense, but direct use of GSH as a therapeutic agent is limited because of its unfavorable biochemical and pharmacokinetic properties.

Figure 2:
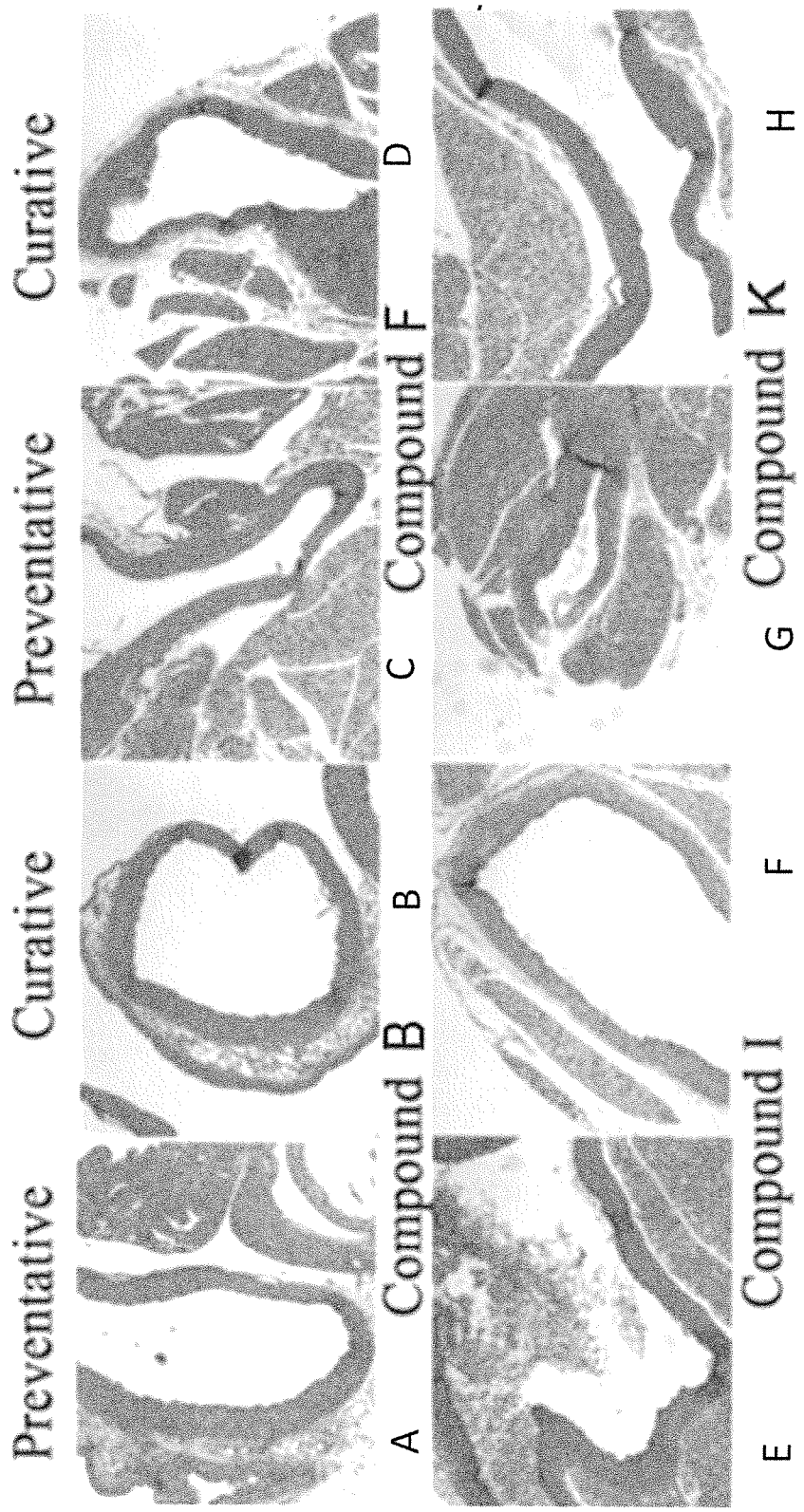
FIGS. 2A-2H are photographs of 'curative' and 'preventive' histopathology of arterial vessels in compounds B, F, I, and K.

It should also be understood that any of the above compounds can be used individually and in any combination to achieve desired effects. Any of these compounds alone or together prevent damage or shedding of existing glycocalyx layers as well as provide any of the functionality described above. The compounds can be administered orally and preferably in a single dosage form. The dose for any of the compounds can 5 mg to 750 mg (per 70 kg average human weight). In the preferred combination, the dose can be 50 mg FTX-214, 50 mg FTX-218, and 50 mg FTX-219 (effective dose) up to 750 mg FTX-214, 750 mg FTX-218, and 750 mg FTX-219 (maximum tolerated dose). A 50 mg dose proved to prevent or reverse the disruption of the glycocalyx as evidenced by plaque formation of reversion, as shown in FIGS. 2A-2H (B; FTX-226-4+FTX-229+FTX-214; F: FTX-224-2+FTX-216+FTX-214; I: FTX-216+FTX-214+FTX-218; and K: FTX-214+FTX-218+FTX-219).

The present invention generally provides for a method of treating multiple disease causes, by administering a combination therapeutic to an individual, and targeting multiple causes of a disease. The combination therapeutic has multiple components necessary to target each underlying cause of a disease. Many diseases (such as CVD, cancer, diabetes, or any other disease described below) have multiple mechanisms involved in their presentation. For example, the causes of the disease can include glycocalyx disruption, inflammation, and oxidative damage. In order to treat this disease, the combination therapeutic can include a component that can target glycocalyx disruption, a component that can target inflammation, and a component that can target oxidative damage. The multiple components can be in a single poly pill. One example of the combination therapeutic is the glycocalyx restoring and maintaining compound of the combination of FTX-214, FTX-218, and FTX-219 described above. Previously, diseases were treated just by their symptoms and not their underlying causes, or a single composition was given to treat the underlying cause (as with antibiotics). The present invention allows for multiple components to be administered (preferably within a single pill) that each target a different cause of disease, making it easier for a patient to take their medicine as well as targeting the root causes of their disease.

The present invention provides for a method of treating multiple disease causes, by administering a glycocalyx restoring and maintaining compound to an individual, restoring the glycocalyx, reversing inflammation, and reversing oxidative damage. The glycocalyx restoring and maintaining compound treats the root cause of a disease, restores the glycocalyx, and maintains the glycocalyx. The glycocalyx restoring and maintaining compound can be any of those described above. Normal blood flow shear is necessary for a balanced shedding and synthesis of the proteoglycan components of the glycocalyx and maintaining the residency of various enzymes and signaling molecules including the antioxidant superoxide dismutase (SOD), anti-inflammatory antithrombin (AT-III), and proteases (thrombin, plasmin, protease-3, and elastase that are important in blood clotting, immunity, and inflammation). Once the balance of these resident enzymes are disrupted, glycocalyx shedding ensues followed by a cascade of pathological events. Thus, the therapeutic approach of the present invention that improves the glycocalyx structure and function also can prevent the pathological processes connected with vascular inflammation. The composition is able to restore the balance of the enzymes above.

More specifically, the disease being treated can be any cardiovascular disease (CVD), as CVD involves disruption of the glycocalyx, inflammation, and oxidative damage resulting in eventual clot formation and travel of the clot to small vessels, resulting in flow disruption (i.e. stroke, etc.). Therefore, the present invention provides for a method of treating CVD, by administering a glycocalyx restoring and maintaining compound to an individual, restoring the glycocalyx, reversing inflammation, and reversing oxidative damage. The CVD being treated can be, but is not limited to, coronary heart disease, myocardial infarction, stroke, hypertension, atrial fibrillation, congestive heart failure, congenital heart condition, peripheral arterial disease, venous thrombosis, deep venous thrombosis, and pulmonary embolism.

The disease being treated with the glycocalyx restoring and maintaining compound can also be any disease with the indications of disrupted glycocalyx, inflammation, and/or oxidative damage. For example, a disrupted glycocalyx can be indicated in damage to the body (as it cushions the plasma membrane and protects it from chemical injury), impaired immunity to infection (as it enables the immune system to recognize and selectively attack foreign organisms), cancer (changes in the glycocalyx of cancerous cells enable the immune system to recognize and destroy them), transplant rejection (it forms the basis for compatibility of blood transfusions, tissue grafts, and organ transplants), cell adhesion issues (it binds cells together so that tissues do not fall apart), inflammation regulation diseases (glycocalyx coating on endothelial walls in blood vessels prevents leukocytes from rolling/binding in healthy states), fertilization issues (as it enables sperm to recognize and bind to eggs), embryonic development issues (as it guides embryonic cells to their destinations), and diabetes. Inflammation can be indicated in plasma cell leukemia, rheumatoid arthritis, multiple myeloma, Lennert syndrome, Castleman's disease, cardiac myxomas, liver cirrhosis, chronic polyarthritis, bacterial and viral meningitis, graft-versus-host reactions, intra-amniotic infections, inflammatory intestinal disease, many cancers and advanced cancers (including pancreatic cancer), encephalitis, decreased gene expression, schizophrenia, depression, bacterial, viral, fungal, parasitic infections, microbial toxins, tissue necrosis, foreign bodies present, immune reaction, acne vulgaris, asthma, autoimmune diseases, celiac disease, chronic prostatitis, glomerulonephritis, hypersensitivities, inflammatory bowel diseases, pelvic inflammatory disease, reperfusion injury, sarcoidosis, transplant rejection, vasculitis, interstitial cystitis, atherosclerosis, allergies, myopathies, leukocyte defects, endometriosis, and multiple sclerosis. Oxidative damage can be indicated in cancer, Parkinson's disease, Alzheimer's disease, atherosclerosis, heart failure, myocardial infarction, fragile X syndrome, sickle cell disease, lichen planus, vitiligo, autism, infection, and chronic fatigue syndrome. It should be understood that the glycocalyx restoring and maintaining compound can not only reverse the diseases listed above but also prevent their occurrence.

Since the glycocalyx restoring and maintaining compound can treat any one of disruption of the glycocalyx, inflammation, and oxidative damage individually or in combination, the present invention also includes the following methods. A method of restoring the glycocalyx is provided by administering the glycocalyx restoring and maintaining compound to an individual and restoring the glycocalyx. A method of reversing inflammation is provided by administering the glycocalyx restoring and maintaining compound to an individual, reversing inflammation, and restoring the glycocalyx. In other words, by reversing inflammation which can be causing disruption and damage of the glycocalyx, the glycocalyx can be restored to normal function. A method of reversing oxidative damage is provided by administering the glycocalyx restoring and maintaining compound to an individual, reversing oxidative damage, and restoring the glycocalyx. In other words, by reversing oxidative damage which can be causing disruption and damage of the glycocalyx, the glycocalyx can be restored to normal function.

The present invention also provides more generally for a method of treating any disease involving a membrane that has a glycocalyx, by administering a glycocalyx restoring and maintaining compound to an individual, restoring the glycocalyx of the membrane, reversing inflammation, and reversing oxidative damage. The glycocalyx restoring and maintaining compound can treat, restore, and maintain any membrane that has a glycocalyx. The membrane can be, but is not limited to, blood vessels, lungs, endometrial linings, digestive tract linings, epithelium, or any other lining in the body. The glycocalyx restoring and maintaining compound can be any of those described above.

Epithelium is one of the four basic types of animal tissue, along with connective tissue, muscle tissue and nervous tissue. Epithelial tissues line the cavities and surfaces of structures throughout the body. Many glands are made up of epithelial cells. Functions of epithelial cells include secretion, selective absorption, protection, transcellular transport and detection of sensation. Cells of epithelial tissue are tightly packed and form a continuous sheet. Epithelial cells line up the cavity of tissues throughout the body and form glands; major layer in mucosal membrane. Most epithelial cells have a fuzz-like coat on the external surface of their plasma membranes called glycocalyx, a glycoprotein-polysaccharide covering that surrounds the cell membranes, including some bacteria. This coating consists of several carbohydrate moieties of membrane glycolipids and glycoproteins, which serve as backbone molecules for support. Generally, the carbohydrate portion of the glycolipids found on the surface of plasma membranes helps these molecules contribute to cell-cell recognition, communication, and intracellular adhesion.

The lining of the mouth, lung alveoli, and kidney tubules all are made of epithelial tissue. The lining of the blood and lymphatic vessels are of a specialized form of epithelium called endothelium. Epithelium lines both the outside (skin) and the inside cavities and lumen of bodies. Epithelial cells in mucosal surfaces are continuously faced with the critical function of forming a protective apical barrier that prevents cellular damage and infection while allowing the exchange of molecules with the extracellular milieu. Loss of barrier function is ascribed to numerous mucosal pathologies, such as dry eye, severe asthma, and inflammatory bowel disease.

The primary functions of epithelial tissues are: (1) to protect the tissues that lie beneath it from radiation, desiccation, toxins, invasion by pathogens, and physical trauma; (2) the regulation and exchange of chemicals between the underlying tissues and a body cavity; (3) the secretion of hormones into the blood vascular system, and/or the secretion of sweat, mucus, enzymes, and other products that are delivered by ducts; and (4) to provide sensation. The glycocalyx restoring and maintaining compound can treat, restore, and maintain any epithelial tissue that has a glycocalyx.

The glycocalyx restoring and maintaining compound can also be administered in combination with other therapeutic agents to treat specific diseases and conditions. The therapeutic agents can include, but are not limited to, nonsteroidal anti-inflammatory drugs (NSAIDS) such as, but not limited to, acetaminophen, salicylates (aspirin, diflunisal, salsalate), acetic acid derivatives (indomethacin, ketorolac, sulindac etodolac, diclofenac, nabumetone), propionic acid derivatives (ibuprofen, naproxen, flurbiprofen, ketoprofen, oxaprozin, fenoprofen, loxoprofen), fenamic acid derivatives (meclofenamic acid, mefenamic acid, flufenamic acid, tolfenamic acid), oxicam (enolic acid) derivatives (piroxicam, meloxicam, tenoxicam, droxicam, lornoxicam, isoxicam), arylalkanoic acid derivatives (tolmetin); or selective COX-2 inhibitors (celecoxib, rofecoxib, valdecoxib, parecoxib, lumiracoxib, etoricoxib, firocoxib). The therapeutic agent can also be generally from the classes antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins. These therapeutic agents can be administered at the same time, before, or after the glycocalyx restoring and maintaining compound, they can be in separate or the same dosage form, and they can have different or the same release profiles.

In other diseases, it can be advantageous to disrupt the glycocalyx. For example, in treating cancer, a glycocalyx disrupting compound can be administered with an immune potentiator in order to disrupt the glycocalyx and allow for an immune attack by the body (potentiated by the immune potentiator especially in immune deficient individuals) to reduce and destroy any cancer cells.

Receptors are imbedded in and pass through the glycocalyx. Transmembrane glycoprotein receptors are an integral part of a membrane bound receptor. Disruption of the glycocalyx, can render dysfunctional and structurally disrupt these membrane bound receptors. The glycocalyx restoring and maintaining compound can restore the glycocalyx and restore structural integrity and function to those receptors. Therefore, the present invention provides for a method of restoring the structural and functional integrity of receptors in the glycocalyx by administering the glycocalyx restoring and maintaining compound to an individual, and restoring structural integrity and function of receptors imbedded in and passing through the glycocalyx.

The receptors in the glycocalyx can be for various antigens and antibodies, both polyclonal and monoclonal. By restoring the receptor integrity, the total systemic effect of the ligand (i.e. antigen or antibody) can be restored to a healthy condition and effectively increased. The activity can be metabolic, immunologic, or any other activity that is receptor-controlled. The response of antibodies can be potentiated with administration of the glycocalyx restoring and maintaining compound because the receptors they bind to are restored.

Therefore, the present invention provides for a method of restoring the glycocalyx and receptors therein and potentiating drug response, by administering the glycocalyx restoring and maintaining compound and an antibody to an individual suffering from disease, restoring the glycocalyx, restoring receptors in the glycocalyx, and potentiating the response of the antibody. The present invention also provides for a composition for treating diseases including the glycocalyx restoring and maintaining compound and an antibody. The components of this combination can be in the same dosage form or in different dosage forms, and can be administered with different or the same release profiles.

The disease being treated can be any disease or condition for which an antibody can be used to treat, such as, but not limited to, autoimmune diseases, cancers, metabolic disorders, or infectious diseases. The receptor being restored can be any receptor that the particular antibody binds to or otherwise interacts with.

The antibody can generally be any suitable monoclonal or polyclonal antibody, such as, but not limited to, 3F8, 8H9, abagovomab, abciximad, abrilumab, actoxumab, adalimumab, adecatumumab, aducanumab, afelimomab, afutuzumab, alacizumab pegol, ALD518, alemtuzumab, alirocumab, altumomab pentetate, amatuximab, anatumomab mafenatox, anifrolumab, anrukinzumab, apolizumab, arcitumomab, aselizumab, atinumab, atlizumab, atorolumumab, bapineuzumab, basiliximab, bavituximab, bectumomab, belimumab, benralizumab, bertilimumab, besilesomab, bevacizumab, beziotoxumab, biciromab, bimagrumab, bivatuzumab mertansine, blinatumomab, blosozumab, brentuximab vedotin, briakinumab, brodalumab, canakinumab, cantuzumab mertansine, cantuzumab ravtansine, caplacizumab, capromab pendetide, carlumab, catumaxomab, cBR96-doxorubicin immunoconjugate, CC49, cedelizumab, certolizumab pegol, cetuximab, Ch.14.18, citatuzumab bogatox, cixutumumab, clazakizumab, clenoliximab, clivatuzumab tetraxetan, cnatumumab, concizumab, CR6261, crenezumab, dacetuzumab, daclizumab, dalotuzumab, daratumumab, demcizumab, denosumab, detumomab, dinutuximab, diridavumab, dorlimomab aritox, drozitumab, duligotumab, dupilumab, durvalumab, dusigitumab, ecromeximab, eculizumab, edobacomab, edrecolomab, efalizumab, efungumab, eldelumab, elotuzumab, elsilimomab, emibetuzumab, enavatuzumab, enfortumab vedotin, enlimomab pegol, enokizumab, enoticumab, ensituximab, epitumomab cituxetan, epratuzumab, erlizumab, ertumaxomab, etaracizumab, etrolizumab, evinacumab, evolocumab, exbivirumab, fanolesomab, faralimomab, farletuzumab, fasinumab, FBTA05, felvizumab, fezakinumab, ficlatuzumab, figitumumab, flanvotumab, fletikumab, fontolizumab, foralumab, forvirumab, fresolimumab, fluranumab, futuximab, galiximab, ganitumab, gantenerumab, gavilimomab, gemtuzumab ozogamicin, gevokizumab, girentuximab, glembatumumab vedotin, golimumab, gomiliximab, guselkumab, ibalizumab, ibritumomab tiuxetan, icrucumab, igovomab, IMAB362, imciromab, imgatuzumab, inclacumab, indatuximab ravtansine, infliximab, inolimomab, inotuzumab ozogamicin, intetumumab, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, lifastuzumab vedotin, ligelizumab, lintuzumab, lirilumab, lodelcizumab, lorvotuzumab, lorvotuzumab mertansine, lucatumumab, lulizumab pegol, lumiliximab, mapatumumab, margetuximab, maslimomab, matuzumab, mavrilimumab, mepolizumab, metelimumab, milatuzumab, minretumomam, mitumomab, mogamulizumab, morolimumab, motavizumab, moxetumomab pasudotox, muromonab-CD3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, obiltoxaximab, ocaratuzumab, ocrelizumab, odulimomab, ofatumumab, olaratumab, olokizumab, omalizumab, onartuzumab, ontuxizumab, oportuzumab monatox, oregovomab, orticumab, otelixizumab, otlertuzumab, oxelumab, ozanezumab, ozoralizumab, pagibaximab, palivizumab, panitumumab, pankomab, panobacumab, parsatuzumab, pascolizumab, pateclizumab, patritumab, pembrolizumab, pemtumomab, perakizumab, pertuzumab, pexelizumab, pidilizumab, pinatuzumab vedotin, pintumomab, placulumab, polatuzumab vedotin, ponezumab, priliximab, pritoxaximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samilizumab, sarilumab, satumomab pendetide, secukinumab, seribantumab, setoxaximab, sevirumab, SGN-CD19A, SGN-CD33A, sibrotuzumab, sifalimumab, siltuximab, simtuzumab, siplizumab, sirukumab, sofituzumab vedotin, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tarextumab, tefibazumab, telimomab aritox, tenatumomab, teneliximab, teplizumab, teprotumumab, TGN1412, ticilimumab, tigatuzumab, tildrakizumab, TNX-650, tocilizumab, toralizumab, tositumomab, tovetumab, tralokinumab, trastuzumab, TRBS07, tregalizumab, tremelimumab, tucotuzumab celmoleukin, tuvirumab, ublituximab, urelumab, urtoxazumab, ustekinumab, vantictumab, vapaliximab, varlilumab, vatelizumab, vedolizumab, veltuzumab, vepalimomab, vesencumab, volociximab, vorsetuzumab mafodotin, votumumab, zalutumumab, zanolimumab, zatuximab, ziralimumab, or zolimimab aritox.

One particular receptor whose integrity can be restored by the glycocalyx restoring and maintaining compound is the LDL receptor, which mediates LDL endocytosis in the liver, the major route of LDL clearance from circulation. It is desired to reduce LDL levels in individuals with high cholesterol and atherosclerosis and other cardiovascular diseases. Proprotein convertase subtilisin/kexin type 9 (PCSK9) plays a critical role in cholesterol metabolism by controlling the levels of LDL particles that circulate in the bloodstream. PCSK9 increases plasma LDL cholesterol by promoting degradation of the LDL receptor. Monoclonal antibody (MAb) anti-PCSK9 (U.S. Pat. No. 8,062,640 to Sleeman, et al., U.S. Pat. Nos. 8,030,457, 8,168,762, U.S. Patent Application Publication Nos. 2011/0027287, 2012/0020975, 2012/0027765, 2012/0213797, and 2012/0251544 to Jackson, et al., WO2011/027257 to Champion, et al. describe various MAb anti-PCSK9's) is used to bind with PCSK9, or a portion(s) thereof, in order to block its mechanism of action. However, the effectiveness of MAb anti-PCSK9 is diminished when there has been disruption of the glycocalyx and in turn disruption of the receptors therein, including the LDL receptor. By administering the glycocalyx restoring and maintaining compound and restoring the glycocalyx, the LDL receptor can be restored as well, increasing receptor binding, and thereby increasing the efficacy of MAb anti-PCSK9 in a patient suffering from cardiovascular disease and lowering LDL levels.

Therefore, the present invention provides for a method of restoring the glycocalyx and receptors therein and potentiating drug response, by administering the glycocalyx restoring and maintaining compound and MAb anti-PCSK9 to an individual suffering from cardiovascular disease, restoring the glycocalyx, restoring LDL receptors in the glycocalyx, and potentiating the response of the MAb anti-PCSK9. The MAb anti-PCSK9 can be any of those described above, as well as bococizumab (Pfizer RN316, described in U.S. Pat. No. 8,080,243 to Liang, et al.). The present invention also provides for a composition for treating cardiovascular diseases including the glycocalyx restoring and maintaining compound and a MAb anti-PCSK9. The components of this combination can be in the same dosage form or in different dosage forms, and can be administered with different or the same release profiles.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intra-arterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A composition comprising a compound or combination of compounds selected from the group consisting of:

FORMULA I

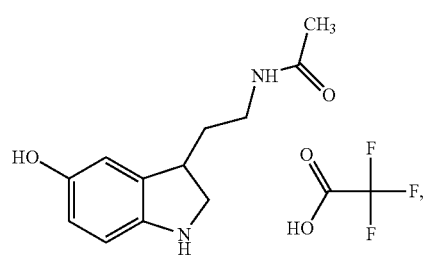

FORMULA III

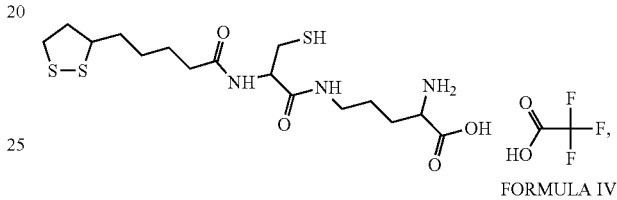

FORMULA IV

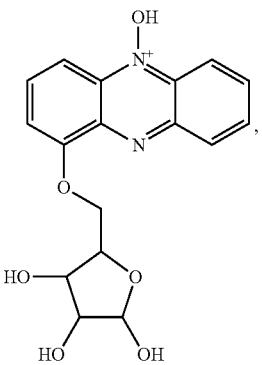

FORMULA V

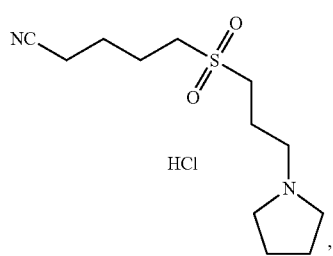

FORMULA VI

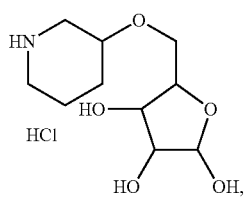

any combination comprising:

FORMULA VII

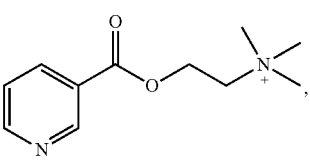

-continued

FORMULA II

FORMULA VIII with at least one different compound or combination of compounds selected from one or more of Formulas I-VIII, and any other combination thereof.

2. A composition comprising a compound or a combination of compounds selected from the group consisting of:

FORMULA I

FORMULA II

FORMULA III

FORMULA IV

FORMULA V

FORMULA VI

FORMULA VII

FORMULA VIII any combination comprising:
  with at least one different compound or combination of compounds selected from one or more of Formulas I-VIII, and
  any other combination thereof, wherein said composition is in an oral dosage form.

3. The composition of claim 2, wherein each compound present in said composition is present in an amount from 5 mg to 750 mg.

4. The composition of claim 1, wherein said composition is in an oral dosage form.

5. The composition of claim 4, wherein each compound present in said composition is present in an amount from 5 mg to 750 mg.

6. The composition of claim 3, wherein each compound present in said composition is present in an amount of 50 mg.

7. A method of restoring and/or maintaining the integrity of a glycocalyx lining of membrane, the method comprising
    administering the composition of claim 1 to an individual.

8. A method of restoring and/or maintaining the integrity of a glycocalyx lining of an endothelial vessel wall, the method comprising administering the composition of claim 2 to an individual.

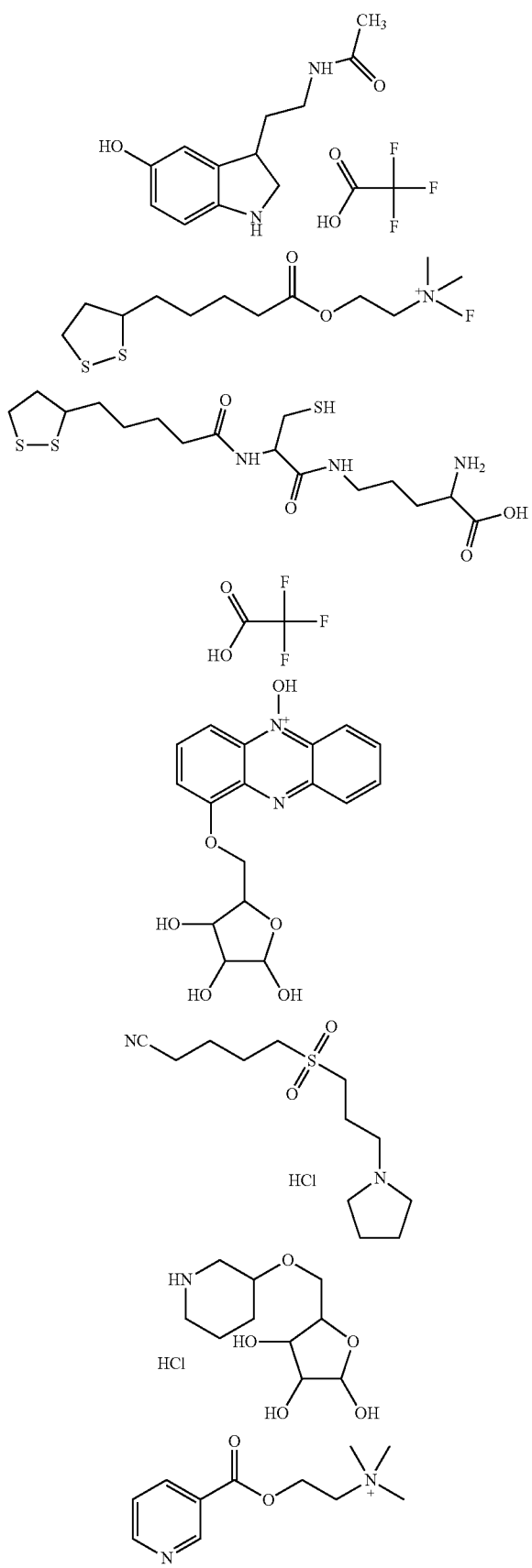

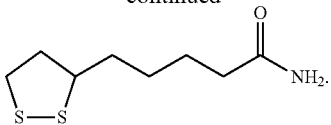

9. The method of claim 7, wherein the composition comprises a combination of compounds of FORMULA I

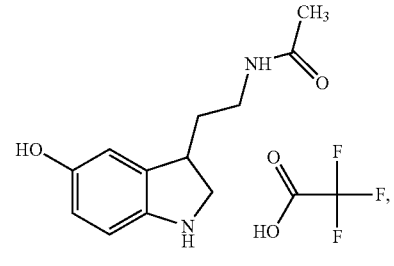

FORMULA I

FORMULA II

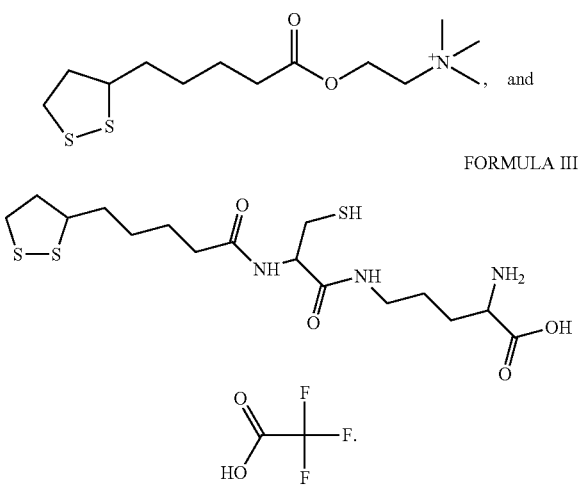

FORMULA III

10. The method of claim 7, wherein said administration comprises restoring the balance of one or more enzymes selected from the group consisting of antioxidant superoxide dismutase (SOD), anti-inflammatory antithrombin (AT-III), thrombin, plasmin, protease-3, elastase, and combinations thereof.

11. The method of claim 7, wherein the individual is suffering from a disease having one or more indications selected from the group consisting of disrupted glycocalyx, inflammation, oxidative damage, and combinations thereof.

12. The method of claim 7, further comprising administering a therapeutic agent selected from the group consisting of antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic agents, caloric agents, water balance agents, enzymes, respiratory tract agents, eye preparations, ear preparations, nose preparations, throat preparations, gold compounds, heavy metal antagonists, hormones and synthetic substitutes, oxytocics, radioactive agents, serums, toxoids, vaccines, skin and mucous membrane agents, smooth muscle relaxants, vitamins, and combinations thereof.

13. The method of claim 7, wherein each compound is administered at a dose ranging from 0.07 mg/kg to 10.71 mg/kg.

14. The method of claim 7, wherein each compound is administered at a dose of about 0.71 mg/kg.

15. The method of claim 7, wherein the individual is suffering from cardiovascular disease (CVD).

16. The method of claim 8, wherein each compound is administered at a dose ranging from 0.07 mg/kg to 10.71 mg/kg.

17. The method of claim 15, wherein each compound is administered at a dose of about 0.71 mg/kg.

18. The method of claim 15, wherein the CVD is selected from the group consisting of coronary heart disease, myocardial infarction, stroke, hypertension, atrial fibrillation, congestive heart failure, congenital heart condition, peripheral arterial disease, venous thrombosis, deep venous thrombosis, and pulmonary embolism.

19. The method of claim 11, wherein the individual is suffering from a disrupted glycocalyx.

20. The method of claim 19, wherein the composition comprises a combination of compounds of

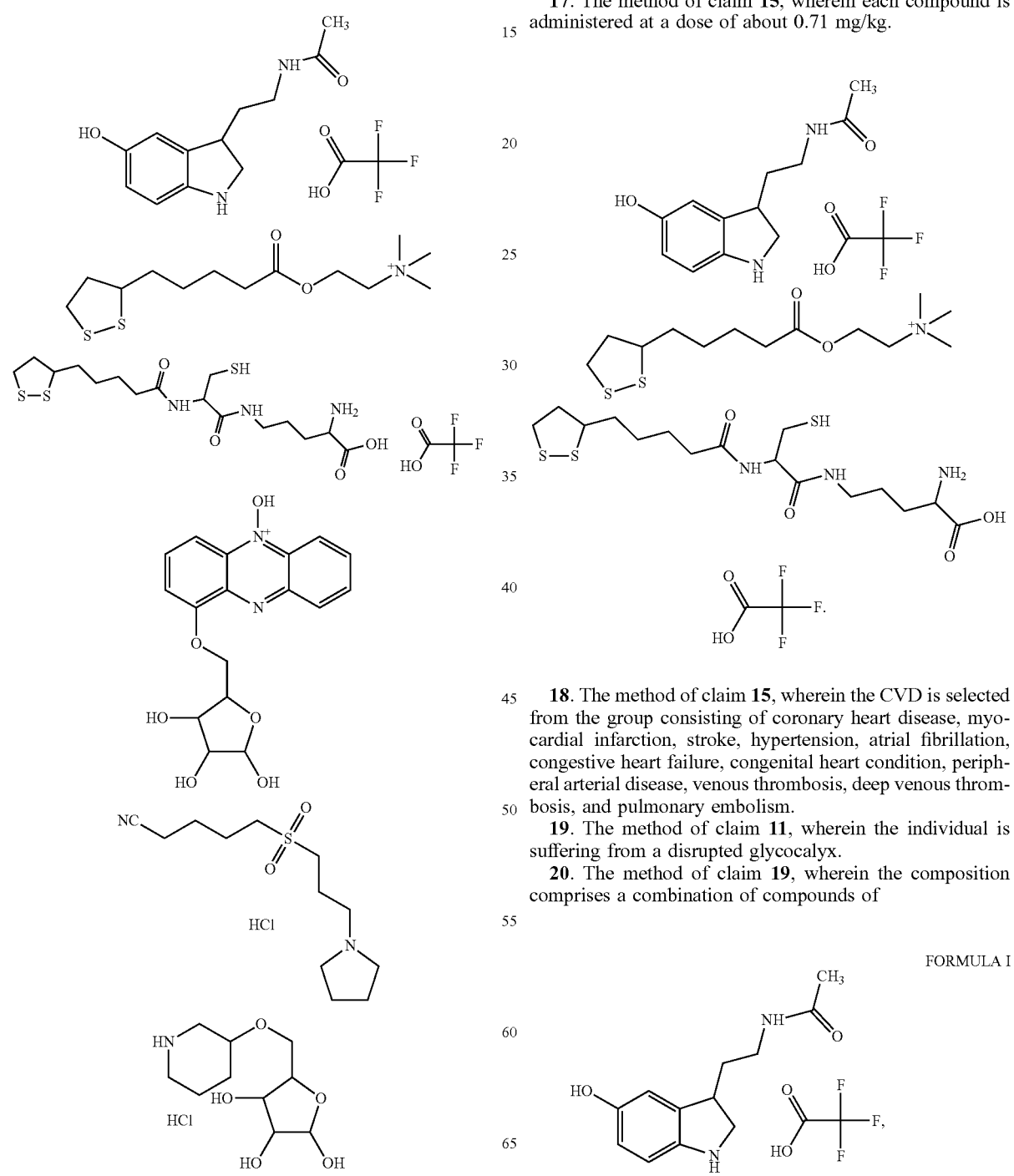

FORMULA II

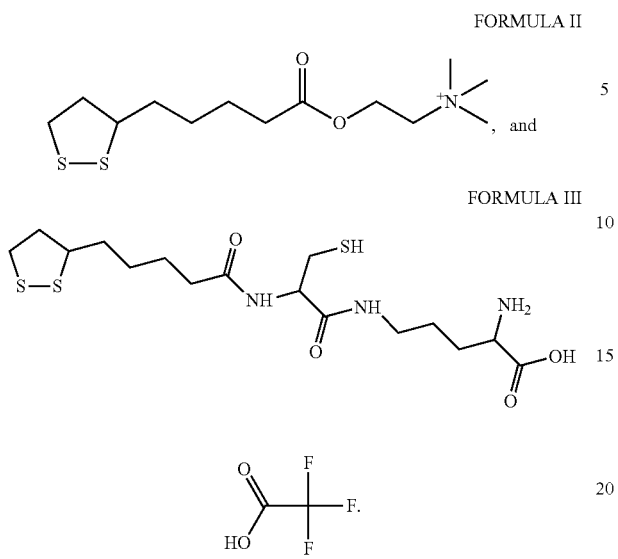

FORMULA III

21. The method of claim 11, wherein the individual is suffering from inflammation.

22. The method of claim 21, wherein the composition comprises a combination of compounds of

FORMULA I

FORMULA II

FORMULA III

23. The method of claim 11, wherein the individual is suffering from oxidative damage.

24. The method of claim 23, wherein the composition comprises a combination of compounds of

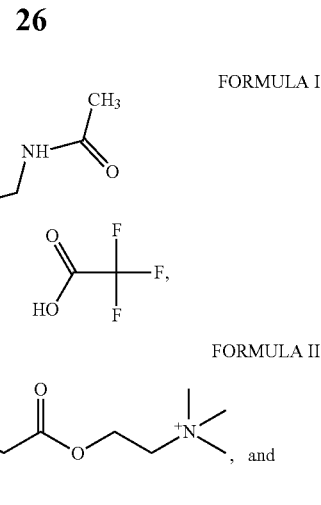

FORMULA I

FORMULA II

FORMULA III

25. The method of claim 7, wherein the method comprises:
   restoring the glycocalyx of a membrane;
   reversing inflammation; and
   reversing oxidative damage.

26. The method of claim 25, wherein the composition comprises a combination of compounds of FORMULA I

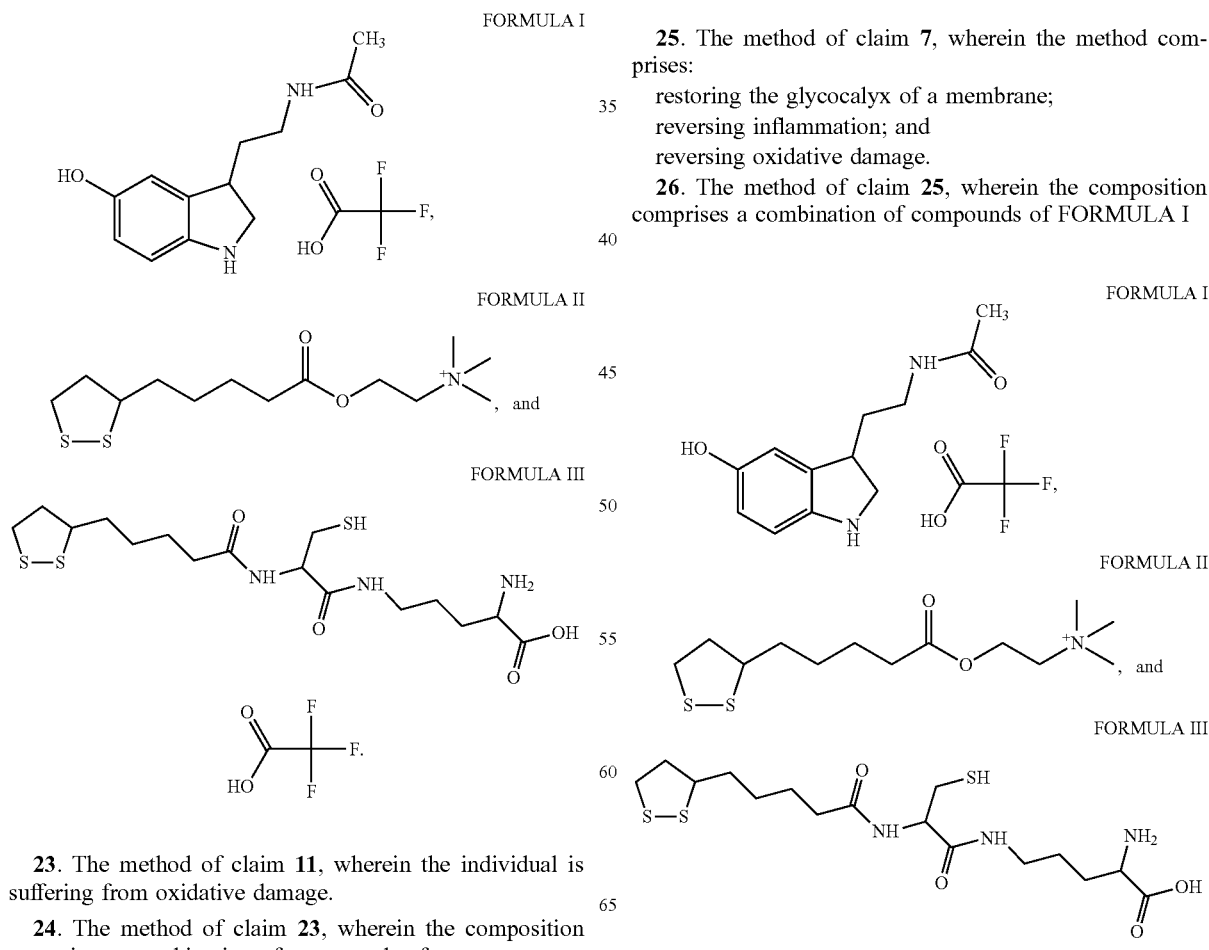

FORMULA I

FORMULA II

FORMULA III

27. The method of claim 25, wherein the membrane is selected from the group consisting of glands, mouth linings, lung alveoli, kidney tubules, ocular surfaces, blood vessels, lungs, endometrial linings, and digestive tract linings.

28. The composition of claim 1, wherein the composition comprises:

FORMULA I

29. The composition of claim 1, wherein the composition comprises:

30. The composition of claim 1, wherein the composition comprises:

FORMULA IV

31. The composition of claim 1, wherein the composition comprises:

FORMULA V

32. The composition of claim 1, wherein the composition comprises:

FORMULA VI

33. The composition of claim 1, wherein the composition comprises:

FORMULA III

FORMULA VII

34. The method of claim 7, wherein the method comprises administering a composition comprising:

FORMULA I

35. The method of claim 7, wherein the method comprises administering a composition comprising:

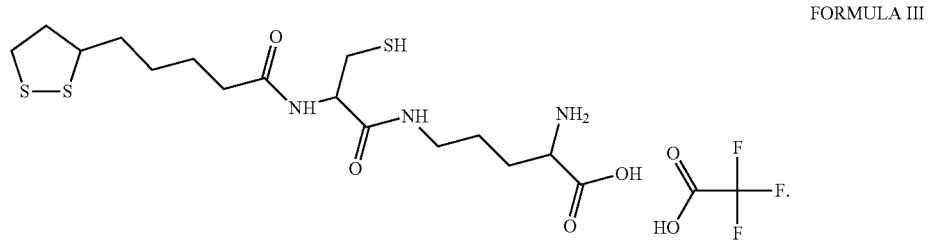

FORMULA III

36. The method of claim 7, wherein the method comprises administering a composition comprising:

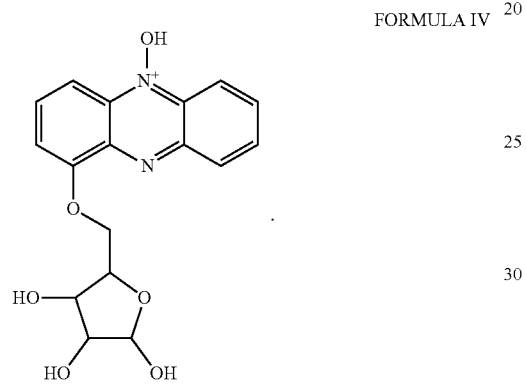

FORMULA IV

37. The method of claim 7, wherein the method comprises administering a composition comprising:

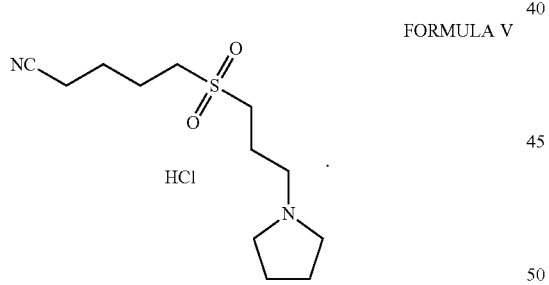

FORMULA V

38. The method of claim 7, wherein the method comprises administering a composition comprising:

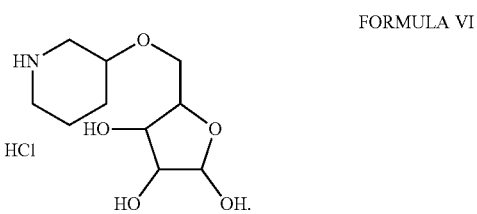 [SMILES: Cl ; OC1OC(COC2CCCNC2)C(O)C1O]

FORMULA VI

39. The method of claim 7, wherein the method comprises administering a composition comprising:

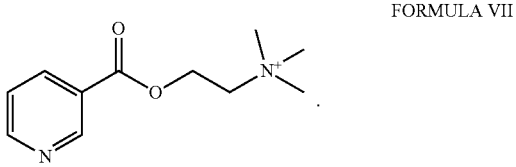

FORMULA VII

40. The method of claim 25, wherein at least two compounds are administered to produce a synergistic effect in:
 restoring the glycocalyx of the membrane;
 reversing inflammation; and/or
 reversing oxidative damage.

41. The method of claim 25, wherein at least three compounds are administered to produce a synergistic effect in:
 restoring the glycocalyx of the membrane;
 reversing inflammation; and/or
 reversing oxidative damage.

* * * * *